(12) United States Patent
Tashiro et al.

(10) Patent No.: US 7,846,313 B2
(45) Date of Patent: Dec. 7, 2010

(54) CONTROLLER FOR GAS CONCENTRATION SENSOR

(75) Inventors: Kenji Tashiro, Susuno (JP); Kazutaka Hattori, Okazaki (JP)

(73) Assignee: Toyota Jidosha Kabushiki Kaisha, Toyota-Shi (JP)

( * ) Notice: Subject to any disclaimer, the term of this patent is extended or adjusted under 35 U.S.C. 154(b) by 546 days.

(21) Appl. No.: 12/005,266

(22) Filed: Dec. 27, 2007

(65) Prior Publication Data

US 2008/0109148 A1    May 8, 2008

Related U.S. Application Data

(62) Division of application No. 10/825,293, filed on Apr. 16, 2004, now Pat. No. 7,393,441.

(30) Foreign Application Priority Data

Apr. 23, 2003   (JP)   ............................. 2003-118337
Aug. 1, 2003    (JP)   ............................. 2003-285183

(51) Int. Cl.
    *G01N 27/407*   (2006.01)
(52) U.S. Cl. .................. 204/406; 204/424; 123/688
(58) Field of Classification Search ................ 204/406, 204/424, 425; 205/785; 73/23.31, 23.32
    See application file for complete search history.

(56) References Cited

U.S. PATENT DOCUMENTS

| 4,112,893 A | 9/1978 | Anzai |
| 4,543,176 A | 9/1985 | Harada et al. |
| 5,405,521 A * | 4/1995 | Nakamori et al. ............ 204/425 |
| 5,547,552 A * | 8/1996 | Hasegawa et al. ........... 204/406 |
| 5,833,836 A | 11/1998 | Takami et al. |
| 5,869,744 A * | 2/1999 | Suzuki et al. .............. 73/23.32 |
| 6,073,083 A | 6/2000 | Schnaibel et al. |
| 6,120,677 A | 9/2000 | Yamada et al. |
| 6,214,207 B1 | 4/2001 | Miyata et al. |
| 6,468,478 B1 | 10/2002 | Honda |
| 6,578,563 B2 | 6/2003 | Hada et al. |

FOREIGN PATENT DOCUMENTS

| EP | 0 822 326 A2 | 2/1998 |
| EP | 0 841 562 A2 | 5/1998 |
| EP | 1 001 261 A1 | 5/2000 |
| JP | 10-048180 A | 2/1998 |
| JP | 10-142194 A | 5/1998 |
| JP | 2000-028575 A | 1/2000 |

OTHER PUBLICATIONS

Sep. 10, 2010 Office Action issued in U.S. Appl. No. 12/005,265.

* cited by examiner

*Primary Examiner*—Kaj K Olsen
(74) *Attorney, Agent, or Firm*—Oliff & Berridge, PLC (57) ABSTRACT

An oxygen sensor is employed for determining whether the exhaust air-fuel ratio is rich or lean. A voltage is applied to the oxygen sensor at device impedance calculation intervals to calculate device impedance. After device impedance calculation, a reverse voltage is applied to the oxygen sensor with a view toward promptly negating the influence of voltage application on the sensor output. Subsequently, the sensor output of the oxygen sensor is sampled at sampling time intervals until it is concluded that the device impedance calculation period is over.

1 Claim, 9 Drawing Sheets

CONTROLLER FOR GAS CONCENTRATION SENSOR

This is a Divisional of application Ser. No. 10/825,293, filed Apr. 16, 2004, now U.S. Pat. No. 7,393,441 which in turn claims the benefit of Japanese Patent Application Nos. JP2003-118337 and JP2003-285183, filed Apr. 23, 2003 and Aug. 1, 2003, respectively. The entire disclosures of the prior applications are hereby incorporated by reference herein in their entirety.

BACKGROUND OF THE INVENTION

1. Field of the Invention

The present invention relates to a controller for a gas concentration sensor, and more particularly to a gas concentration sensor controller that is suitable for the control of a gas concentration sensor installed in an internal-combustion engine's exhaust path.

2. Background Art

As disclosed by Japanese Patent JP-A No. 28575/2000, there is a conventionally known device that includes an oxygen sensor installed in an internal-combustion engine's exhaust path. The oxygen sensor for this device generates an output in accordance with the oxygen concentration in an exhaust gas that flows in the exhaust path. There is a correlation between the oxygen concentration in the exhaust gas and the exhaust air-fuel ratio. With the conventional device, it is therefore possible to obtain the information about the exhaust air-fuel ratio in accordance with the oxygen sensor output.

The above device is capable of detecting the device impedance of the oxygen sensor by varying the voltage V0, which is applied to the oxygen sensor, from a reference voltage to a sweep voltage. If a $\Delta V0$ change occurs in the applied voltage V0, the associated current I changes by $\Delta I$, which corresponds to the device impedance Rs. Therefore, the above conventional device calculates the device impedance Rs in accordance with the voltage change $\Delta V0$ and current change $\Delta I$, which arise when the applied voltage V0 changes from the reference voltage to the sweep voltage.

As described above, the above conventional device acquires the information about the exhaust air-fuel ratio in accordance with the oxygen sensor's output, and detects the device impedance by applying the sweep voltage to the oxygen sensor. While the sweep voltage is applied to the oxygen sensor, the output value of the oxygen sensor is affected by the sweep voltage. Therefore, while the sweep voltage is applied, the oxygen sensor's output does not correspond to the exhaust air-fuel ratio.

The oxygen sensor includes an impedance component and a capacitance component. Therefore, the oxygen sensor's output does not revert to a value corresponding to the exhaust air-fuel ratio for some time after the application of the sweep voltage is stopped. Consequently, the above conventional device may erroneously detect the exhaust air-fuel ratio during the time interval between the instant at which the sweep voltage is applied to the oxygen sensor for device impedance detection purposes and the instant at which the influence of the sweep voltage disappears.

SUMMARY OF THE INVENTION

The present invention has been made to solve the above problems and provides a controller for a gas concentration sensor, which is capable of detecting the device impedance of the gas concentration sensor and accurately detecting the information about the exhaust air-fuel ratio.

The above object of the present invention is achieved by a controller for a gas concentration sensor that generates an output correlating with the oxygen concentration in a detected gas. The controller includes an impedance detection unit for applying an impedance detection voltage to the gas concentration sensor to detect a device impedance of the gas concentration sensor. The controller also includes a reverse voltage application unit for applying the same voltage as generated by the gas concentration sensor itself or a voltage that shifts from the same voltage toward an opposite direction against a direction of the impedance detection voltage to the gas concentration sensor for a specified period of time after the impedance detection voltage is applied to the gas concentration sensor.

The above object of the present invention is also achieved by a controller for a gas concentration sensor that generates an output correlating with the oxygen concentration in a detected gas. The controller includes an impedance detection unit for applying an impedance detection voltage to the gas concentration sensor to detect a device impedance of the gas concentration sensor. The controller also includes a data invalidation unit for invalidating the output of the gas concentration sensor for a specified period of time after the impedance detection voltage is applied to the gas concentration sensor.

The above object of the present invention is also achieved by a controller for a gas concentration sensor that generates an output correlating with the oxygen concentration in a detected gas. The controller includes an impedance detection unit for applying an impedance detection voltage to the gas concentration sensor at specified time intervals to detect a device impedance of the gas concentration sensor. The controller further includes an impedance detection time interval setup unit for increasing the specified time intervals with an increase in the device impedance.

Other objects and further features of the present invention will be apparent from the following detailed description when read in conjunction with the accompanying drawings.

BEST MODE OF CARRYING OUT THE INVENTION

Embodiments of the present invention will now be described with reference to the accompanying drawings. Like elements in the drawings are designated by like reference numerals and will not be described again.

First Embodiment

Circuit Configuration Description

Figure 1:
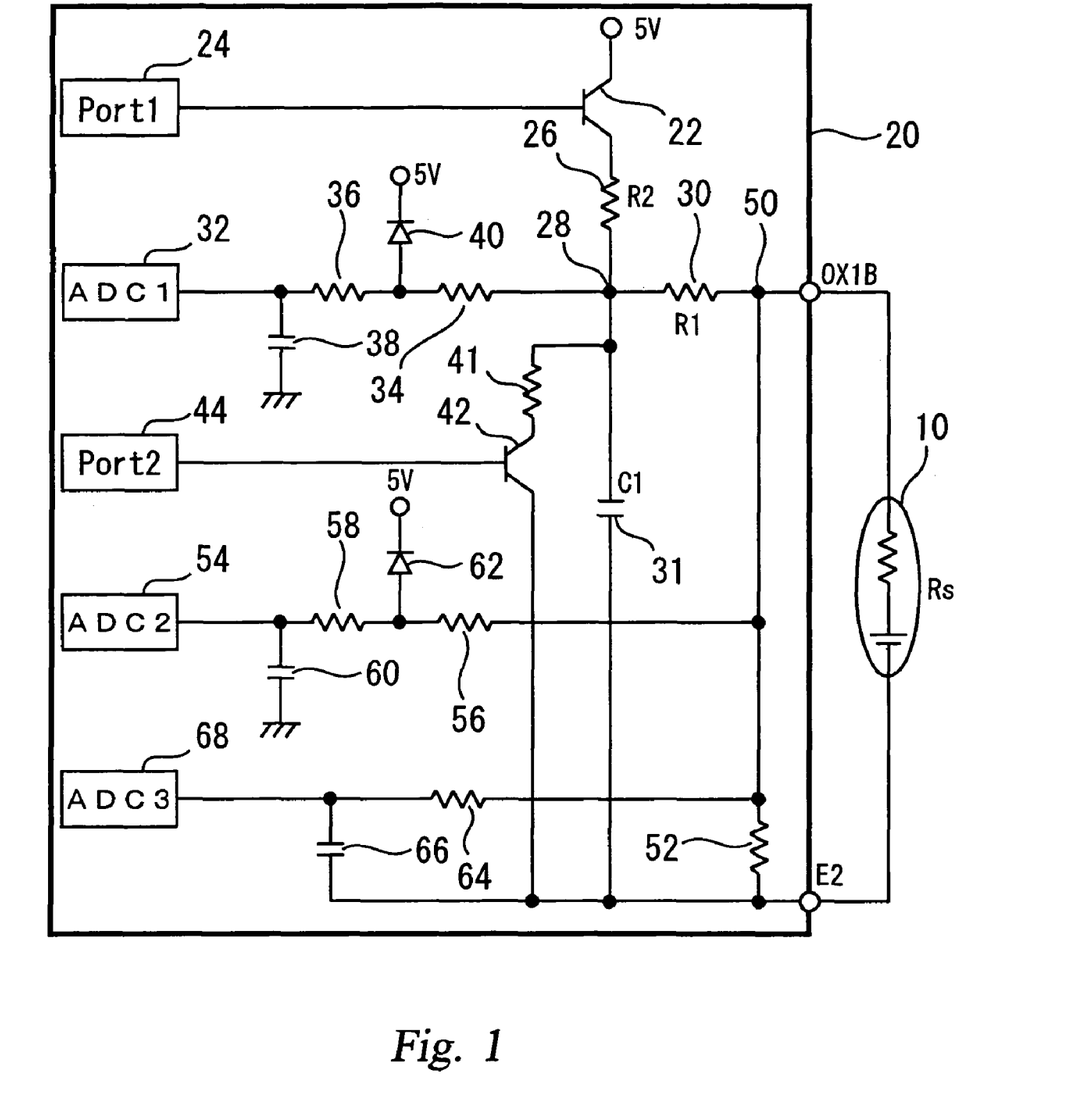
FIG. 1 is a diagram showing a configuration of a first embodiment of the present invention.

FIG. 1 is a diagram showing a configuration of a first embodiment of the present invention. As shown in FIG. 1, the system according to the first embodiment includes an oxygen sensor 10 and an ECU (Electronic Control Unit) 20. In the present embodiment, the oxygen sensor 10 is installed in the exhaust path of an internal-combustion engine to generate a sensor output in accordance with the oxygen concentration in exhaust gas. More specifically, the oxygen sensor generates a sensor output that indicates whether exhaust air-fuel ratio is rich or lean.

In FIG. 1, the oxygen sensor 10 is equivalently indicated as an element that includes an impedance component and an electromotive force component. In other words, the oxygen sensor 10 is an electromotive sensor that generates a voltage in accordance with the oxygen concentration in a detected gas. In the present embodiment, the oxygen sensor 10 is connected to the ECU 20 so that the OX1B terminal is on a high-voltage side, and that the E2 terminal is on a low-voltage side. The ECU 20 monitors the voltage generated between the OX1B terminal and E2 terminal to judge whether the exhaust air-fuel ratio is rich or lean.

The device impedance Rs of the oxygen sensor 10 has such a temperature characteristic that the higher the temperature of the oxygen sensor 10, the smaller the value of the device impedance Rs. To permit the oxygen sensor 10 to function normally, it is necessary to maintain the oxygen sensor 10 at an active temperature. Since the temperature of the oxygen sensor 10 correlates with the device impedance Rs, being able to detect the device impedance Rs accurately is useful in order to control the temperature to the above active temperature. Further, if the device impedance Rs can be accurately detected, it is possible to perform a diagnostic check on the oxygen sensor 10 based on the detected value. As described above, it is required that the device impedance Rs of the oxygen sensor 10 be accurately detected.

To comply with the above requirements, the ECU 20 is capable of accurately detecting the device impedance Rs of the oxygen sensor 10. The ECU 20 for use in the present embodiment is a unit that is capable of acquiring the information about the exhaust air-fuel ratio and detecting the device impedance Rs of the oxygen sensor 10 in accordance with the voltage generated by the oxygen sensor 10 (the voltage developed between the OX1B terminal and E2 terminal). The circuit configuration and functionality of the ECU 20 will now be described in detail.

The ECU 20 includes a first switching device 22. A constant voltage (input voltage) of 5 V is supplied to the first switching device 22. The gate of the first switching device 22 communicates with a first port 24. The ECU 20 issues an ON command to the first port 24 as needed to turn ON the first switching device 22.

The first switching device 22 is connected to a first sampling point 28 via a second resistor 26. The first sampling point 28 is electrically connected to OX1B external terminal of the ECU 20 via a first resistor 30 and electrically connected to the E2 external terminal of the ECU 20 via a first capacitor 31.

The first sampling point 28 is connected to a first analog-to-digital converter (ADC1) 32 via a filter circuit having a small time constant. The filter circuit comprises two series-connected resistors 34, 36 and a capacitor 38, which is positioned between an input terminal of the first analog-to-digital converter 32 and a ground wire. A diode 40 is connected between the two resistors 34, 36 to maintain the potentials for their joints at a voltage below 5 V for protection purposes.

The first analog-to-digital converter 32 is capable of converting an analog signal, which is supplied to its input terminal, to a digital signal. The potential of the first sampling point 28 is supplied to the input terminal of the first analog-to-digital converter 32 via the aforementioned filter circuit having a small time constant. Therefore, the first analog-to-digital converter 32 can accurately digitize and output the potential of the first sampling point 28 even when it varies at a high frequency. As detailed later, the ECU 20 recognizes the digital signal generated by the first analog-to-digital converter 32 in a specified situation as the potential of the first sampling point 28, and uses it in a detection process for the device impedance Rs.

Further, a second switching device 42 is connected to the first sampling point 28 via a third resistor 41. The gate of the second switching device 42 is connected to a second port 44. The ECU 20 issues an ON command to the second port 44 as needed to turn ON the second switching device 42. Therefore, when the ECU 20 issues an ON command to the second port 44, the first sampling point 28, is electrically connected to the E2 external terminal via the third resistor 41.

In the ECU 20, a second sampling point 50 is formed between the first resistor 30 and the OX1B external terminal. The second sampling point 50 is connected to one end of an output detection resistor 52, which is positioned parallel to the oxygen sensor 10. The impedance of the output detection resistor 52 is sufficiently greater than the device impedance Rs of the oxygen sensor 10. Therefore, if no input voltage is supplied to the second sampling point 50 (the first switching device 22 is OFF), a voltage equivalent to the electromotive force of the oxygen sensor 10 is generated at the second sampling point 50. If, on the other hand, an input voltage is supplied to the second sampling point 50 (the first switching device 22 is ON), a voltage equivalent to the product of the current I flowing to the oxygen sensor 10 and the device impedance Rs is generated at the second sampling point 50.

A second analog-to-digital converter (ADC2) 54 is connected to the second sampling point 50 via a filter circuit having a small time constant. The filter circuit comprises two series-connected resistors 56, 58 and a capacitor 60, which is positioned between an input terminal of the second analog-to-digital converter 54 and a ground wire. A diode 62 is connected between the two resistors 56, 58 to maintain the potentials for their joints at a voltage below 5 V for protection purposes.

The second analog-to-digital converter 54 is capable of converting an analog signal, which is supplied to its input terminal, to a digital signal. The input terminal of the second analog-to-digital converter 54 is connected to the second sampling point 50 via the aforementioned filter circuit having a small time constant. Therefore, the second analog-to-digital converter 54 can accurately digitize and output the potential of the second sampling point 50 even when it varies at a high frequency. As detailed later, the ECU 20 recognizes the digital signal generated by the second analog-to-digital converter 54 in a specified situation as the potential of the second sampling point 50, and uses it in a detection process for the device impedance Rs.

Further, the second sampling point 50 is connected to a third analog-to-digital converter (ADC3) 68 via a filter circuit, which comprises a resistor 64 and a capacitor 66. The filter circuit, which is positioned before the third analog-to-digital converter 68, has a sufficiently great time constant so that only the low-frequency components of a voltage at the second sampling point 50 are allowed to pass. Therefore, the third analog-to-digital converter 68 can accurately generate a digital signal equivalent of a steady-state voltage at the second sampling point 50 without being affected by noise or the like. As detailed later, the ECU 20 recognizes the digital signal generated by the third analog-to-digital converter 68 in a specified situation as the output signal of the oxygen sensor 10, and uses it in a process for detecting the oxygen concentration in a detected gas.

[ECU Operation Description]

(Process for Detecting the Oxygen Concentration Information)

The ECU 20 turns OFF the first port 24 except in an attempt to detect the device impedance Rs of the oxygen sensor 10. When the first port 24 is OFF, the first switching device 22 turns OFF so that the steady-state potential of the second sampling point 50 is equivalent to the electromotive force of the oxygen sensor 10 (see FIG. 1). In this instance, the output of the third analog-to-digital converter 68 is equal to the sensor output of the oxygen sensor 10. Under such a situation, the ECU 20 detects the digital signal generated by the third analog-to-digital converter 68 at specified time intervals (e.g., at 4 msec intervals), and acquires the information about the oxygen concentration in the exhaust gas in accordance with the detected signal value.

(Process for Calculating the Device Impedance Rs)

Figure 2A:
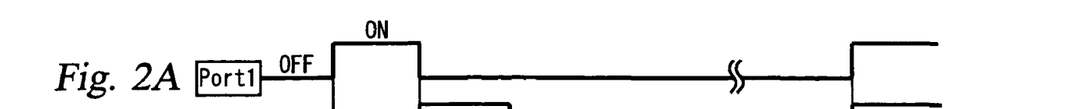
FIGS. 2A, 2B, 2C, 2D, and 2E are timing diagrams illustrating an operation that is performed in the first embodiment of the present invention.
Figure 2B:
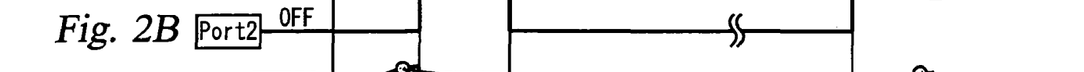
Figure 2C:
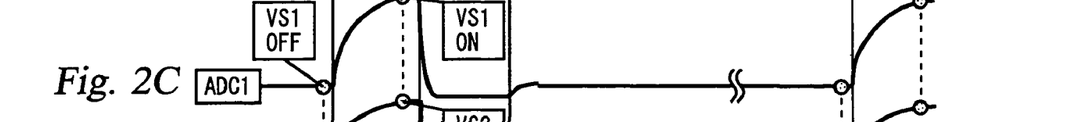
Figure 2D:
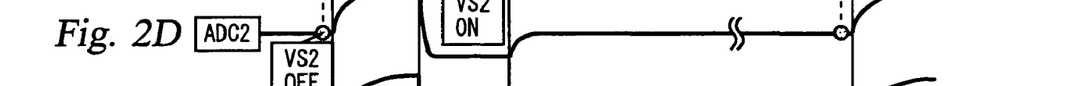
Figure 2E:
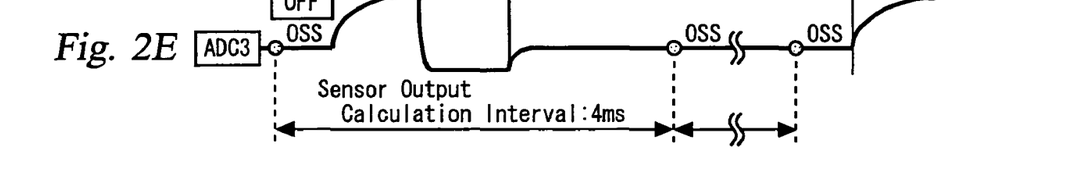

FIGS. 2A to 2E are timing diagrams illustrating the operation that the ECU 20 performs in a mode for calculating the device impedance Rs of the oxygen sensor 10. More particularly, FIGS. 2A and 2B show waveforms of the status of the first port 24 and the second port 44, respectively. FIGS. 2C to 2E show waveforms indicating the changes in the potentials that are supplied to the input terminals of the first to third analog-to-digital converters 32, 54, 68, respectively.

In the mode for calculating the device impedance Rs, the ECU 20 generally turns OFF the second port 44 (see FIG. 2B). In this instance, the second switching device 42 turns OFF so that, inside the ECU 20, only the first capacitor 31 is connected parallel to a series circuit for the first resistor 30 and the sensor device 10. The parallel circuit formed by such elements is hereinafter referred to as the "R1/Rs-C1 parallel circuit". The ECU 20 includes the output detection resistor 52, which is connected parallel to the oxygen sensor 10.

However, the resistance value of the output detection resistor 52 (e.g., 1.5 MΩ) is sufficiently greater than the value of the device impedance Rs of the oxygen sensor 10 (not greater than several tens of kilohms). It is therefore assumed that the existence of the output detection resistor 52 is ignorable.

When the calculation of the device impedance Rs is demanded, the ECU 20 turns ON the first port 24 with the second port 44 left OFF (see FIG. 2A). When the first port 24 turns ON, the first switching device 22 turns ON so that an input voltage of 5 V begins to be applied to the second resistor 26. This voltage passes through the second resistor 26, works on the first sampling point 28, and is applied to the R1/Rs-C1 parallel circuit.

When the above voltage begins to be applied to the first sampling point 28, the potential VS1 at that point subsequently rises in accordance with the time constant τ and finally converges to a value that is determined according to the ratio between the resistance value R2 of the second resistor 26 and the combined resistance value R1+Rs of the first resistor 30 and oxygen sensor 10. In this instance, the resulting convergence value VS1 and the time constant τ are respectively expressed by Equations (1) and (2) shown below.

$$VS1 = 5(R1+Rs)/(R2+R1+Rs) \qquad \text{Equation (1)}$$

$$\tau = C1/\{1/(Rs+R1)+1/R2\} \qquad \text{Equation (2)}$$

In the circuit shown in FIG. 1, the potential VS1 at the first sampling point 28 is supplied to the first analog-to-digital converter 32. Therefore, the output of the first analog-to-digital converter 32 varies in the same manner as the value VS1, which is indicated by Equations (1) and (2). The waveform shown in FIG. 2C shows that the output of the first analog-to-digital converter 32 varies in such a manner after the first port 24 is turned ON.

In a process in which the potential VS1 at the first sampling point 28 varies as described above, the current I flows to the oxygen sensor 10 as indicated by the following equation:

$$I = VS1/(R1+Rs) \qquad \text{Equation (3)}$$

In this instance, the potential VS2 at the second sampling point 50 can be expressed as follows using the current I and device impedance Rs:

$$VS2 = Rs \cdot I \qquad \text{Equation (4)}$$

Since the potential VS1 at the first sampling point 28 varies according to the time constant τ, the current I, which satisfies Equation (3), and the potential VS2 at the second sampling point 50, which satisfies Equation (4), both vary according to the time constant τ. In the circuit shown in FIG. 1, the potential VS2 at the second sampling point 50 is supplied to the second analog-to-digital converter 54. Therefore, the output of the second analog-to-digital converter 54 varies in the same manner as the value VS2, which is expressed by Equations (4) and (2). The waveform shown in FIG. 2D indicates that the output of the second analog-to-digital converter 54 varies in such a manner after the first port 24 is turned ON.

The current I, which flows to the oxygen sensor 10, can be expressed as follows using the potential VS1 at the first sampling point 28, the potential VS2 at the second sampling point 50, and the resistance value R1 of the first resistor 30:

$$I = (VS1-VS2)/R1 \qquad \text{Equation (5)}$$

From Equations (4) and (5), the device impedance Rs can be expressed as follows:

$$Rs = VS2/I \qquad \text{Equation (6)}$$
$$= VS2 \cdot R1/(VS1 - VS2)$$

As described above, in the circuit according to the present embodiment, the device impedance Rs of the oxygen sensor 10 can be calculated from the potentials VS1, VS2 that are developed at the first sampling point 28 and second sampling point 50 after the first port 24 is turned ON. Influence of a leak current or the like which has been existing from before the turning ON of the first port 24 is superposed over the potential VS1 at the first sampling point 28 and the potential VS2 at the second sampling point 50 of after the turning ON of the first port 24. For accurate calculation of the device impedance Rs, therefore, it is preferred that the influence of the leak current or the like be eliminated.

Therefore, the ECU 20 determines the difference ΔVS1 between the potential VS1 prevailing immediately before the first port 24 is turned ON (hereinafter referred to as "VS1OFF") and the potential VS1 prevailing after the first port 24 is turned ON (hereinafter referred to as "VS1ON"), determines the difference ΔVS2 between the potential VS2 prevailing immediately before the first port 24 is turned ON (hereinafter referred to as "VS2OFF") and the potential VS2 prevailing after the first port 24 is turned ON (hereinafter referred to as "VS2ON"), applies the determined differences to Equation (6), and calculates the device impedance Rs using the following equation:

$$Rs = \Delta VS2 \cdot R1/(\Delta VS1 - \Delta VS2) \qquad \text{Equation (7)}$$
$$= (VS2ON - VS2OFF) \cdot R1/$$
$$\{(VS1ON - VS1OFF) - (VS2ON - VS2OFF)\}$$

However, if the influence of the leak current or the like is insignificant and the value VS1OFF is nearly equal to the value VS2OFF, the relationship expressed by Equation (7) need not always be used. In such an instance, the device impedance Rs should be calculated from Equation (6) (while assuming that VS1=VS1ON and that VS2=VS2ON).

As described earlier, the first analog-to-digital converter 32 enables the ECU 20 to detect the potential of the first sampling point 28. Further, the second analog-to-digital converter 54 enables the ECU 20 to detect the potential of the second sampling point 50. Therefore, when the calculation of the device impedance Rs is demanded, the ECU 20 performs the following calculation steps:

(i) Immediately before the first port 24 is turned ON, the ECU 20 detects the output of the first analog-to-digital converter 32 as VS1OFF and the output of the second analog-to-digital converter 54 as VS2OFF.

(ii) Upon termination of the above detection sequence, the ECU 20 turns ON the first port 24.

(iii) When the period required for VS1 to reach its convergence value (e.g., 135 μsec) elapses after the first port is turned ON, the ECU 20 detects the output of the first analog-to-digital converter 32 as VS1ON and the output of the second analog-to-digital converter 54 as VS2ON.

(iv) Upon termination of the above detection sequence, the ECU 20 turns the first port 24 back OFF.

(v) The ECU 20 substitutes the values VS1OFF, VS1ON, VS2OFF, and VS2ON, which are detected in processing steps (i) through (iii) above, into Equation (7) to calculate the device impedance Rs.

[Description of Problems with Calculating the Device Impedance Rs]

Figure 3:
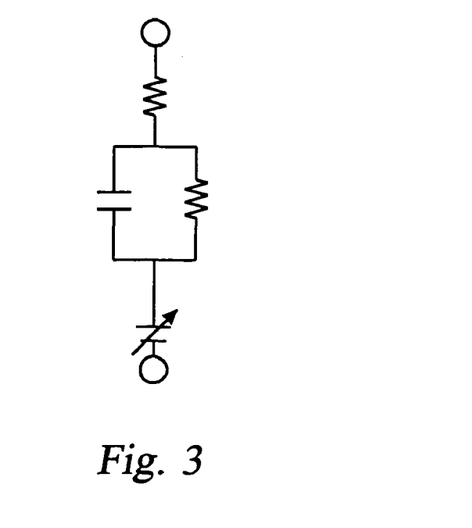
FIG. 3 is an equivalent circuit diagram of an oxygen sensor shown in FIG. 1.

FIG. 3 is an equivalent circuit diagram that strictly illustrates the characteristics of the oxygen sensor 10. As shown in this figure, the oxygen sensor 10 has a capacitance component in addition to an electromotive component and an impedance component. When a voltage is applied to a circuit having such components, an electrical charge is stored in the capacitance component. Before the stored electrical charge is released, the voltage developed across the terminals of the oxygen sensor 10 is higher than the voltage generated by the electromotive component even after the voltage application to the oxygen sensor 10 is stopped. In other words, the sensor output (output voltage) of the oxygen sensor 10 represents an excessive value for the oxygen concentration in the exhaust gas until the electrical charge stored in the capacitance component is released.

Figure 4:
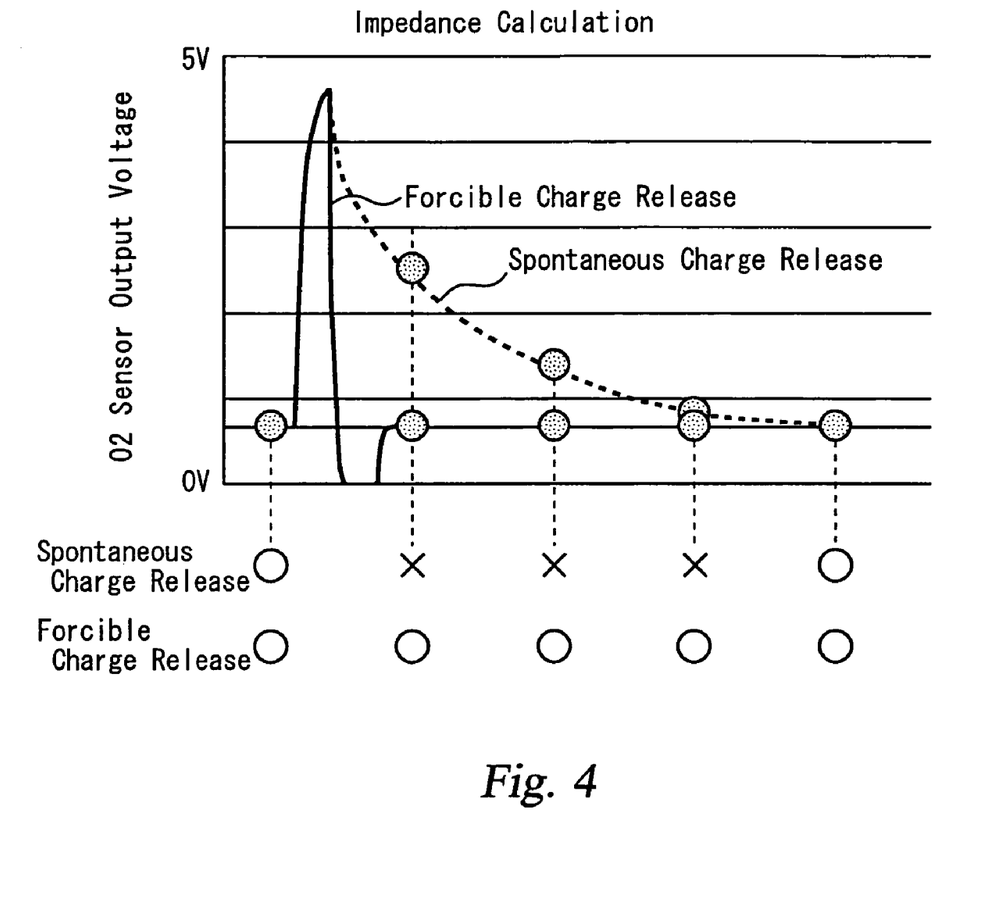
FIG. 4 shows waveforms of sensor output that is generated before and after a voltage is applied to the oxygen sensor shown in FIG. 1.

FIG. 4 shows waveforms of sensor output that is generated before and after a voltage is applied to the oxygen sensor 10 for the purpose of calculating the device impedance Rs. The waveform indicated by a broken line is a sensor output waveform that is obtained when the electrical charge stored in the oxygen sensor 10 is spontaneously released after the first port 24 is turned OFF. The waveform indicated by a solid line is a sensor output waveform that is obtained when the electrical charge stored in the oxygen sensor 10 is forcibly released immediately after the status of the first port 24 is changed from ON to OFF. In the circuit configuration shown in FIG. 1, the electrical charge stored in the oxygen sensor 10 can be forcibly released by turning ON the second port 44, that is, by turning ON the second switching device 42. More specifically, the waveform indicated by the solid line in FIG. 4 is obtained when the second port 44 is ON for only a specified period following the instant at which the status of the first port 24 is changed from ON to OFF.

As indicated by the broken line in FIG. 4, when the electrical charge stored in the oxygen sensor 10 is spontaneously released, the sensor output exceeds the output generated by the oxygen sensor 10 itself for some time (for a period of three samplings in the example shown in FIG. 4) after the voltage application to the oxygen sensor 10 is stopped. Since such an excessive sensor output (output marked X) does not correspond to the oxygen concentration in the exhaust gas, it should not be used as a basis for acquiring the information about oxygen concentration.

On the other hand, when the electrical charge stored in the oxygen sensor 10 is forcibly released, that is, when the second port 44 is ON for a specified period only, the sensor output downs to the ground potential, then converges to the inherent output immediately after the voltage application to the oxygen sensor 10 is stopped, as indicated by the solid line in FIG. 4. In this instance, the sensor output of the oxygen sensor 10 properly corresponds to the oxygen concentration in the exhaust gas immediately after the voltage application to the oxygen sensor 10 is stopped. Therefore, the ECU 20 changes the status of the first port 24 from ON to OFF in order to calculate the device impedance Rs, then forcibly releases the electrical charge stored in the oxygen sensor 10 by keeping the second port 44 ON for a specified period only.

FIGS. 2A and 2B indicate that the second port 44 turns ON at the moment the first port 24 turns OFF, and that the second port 44 turns OFF in a specified period of time. In the present embodiment, the ECU 20 acquires the output of the oxygen sensor 10 that is supplied to the third analog-to-digital converter 68, at 4 msec sampling intervals. FIGS. 2C to 2E indicate that all the input voltages to the first to third analog-to-digital converters 32, 54, 68 converge to the inherent output generated by the oxygen sensor 10 itself within a 4 msec period when the second port is turned ON as described above after the voltage application to the oxygen sensor 10 is started. When the input voltage for the third analog-to-digital converter 68 varies in this manner, all the sensor outputs sampled by the ECU 20 properly correspond to the oxygen concentration in the exhaust gas. As a result, the system according to the present embodiment is always capable of correctly detecting the information about the oxygen concentration in the exhaust gas without being affected by the voltage application for calculating the device impedance Rs after the calculation process for the device impedance Rs terminates.

Figure 5:
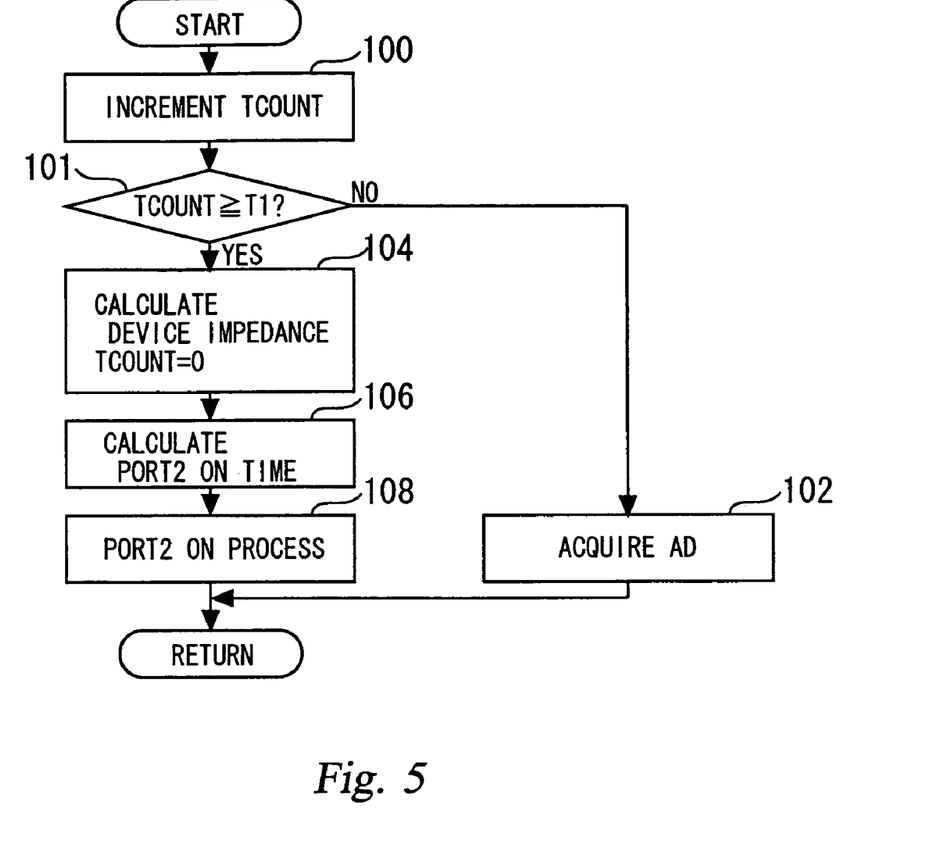
FIG. 5 is a flowchart of a control routine executed in the first embodiment of the present invention.

FIG. 5 is a flowchart illustrating how the ECU 20 executes a control routine in order to implement the above functionality. It is assumed that the routine shown in FIG. 5 is an interrupt routine that is started at time intervals (for instance, of 4 msec) at which the output of the oxygen sensor 10 should be sampled.

The routine shown in FIG. 5 first increments the TCOUNT counter (step 100). The TCOUNT counter is cleared each time the calculation process for the device impedance Rs is performed, and used to count the time elapsed after the clearing.

Next, the count reached by the TCOUNT counter is checked to determine whether it coincides with the device impedance calculation interval T1 (step 101). If it is found in step 101 that TCOUNT is less than T1, the current processing cycle comes to an end after the third analog-to-digital converter 68 acquires the output of the oxygen sensor 10 (AD acquisition) (step 102). According to the above process, the output of the oxygen sensor 10 is acquired at sampling time intervals as the output representing the information about the oxygen concentration in the exhaust gas until TCOUNT reaches to T1 after the calculation process for the device impedance Rs is terminated.

If it is found in step 101 that TCOUNT is greater than or equal to T1, the calculation process for the device impedance Rs is performed at this time point and the TCOUNT counter is cleared to zero (step 104). More specifically, processing steps (i) through (v), which are described earlier, are performed in the calculation process for the device impedance Rs. That is, a voltage is applied to the oxygen sensor 10 with the first port turned ON, and then a process is performed to calculate the device impedance Rs in accordance with the resulting changes in the VS1 and VS2 values.

When the first port 24 turns OFF upon termination of the calculation process for the device impedance Rs, the ON time for the second port 44 is calculated (step 106). As described earlier, the ECU 20 turns ON the second port 44 to forcibly release the electrical charge stored in the oxygen sensor 10 after the device impedance Rs is calculated. In this instance, it is preferred that the second port 44 be turned OFF immediately after termination of forced release of electrical charge. In step 106, therefore, the ON time is set as needed for forced release of electrical charge.

Figure 6:
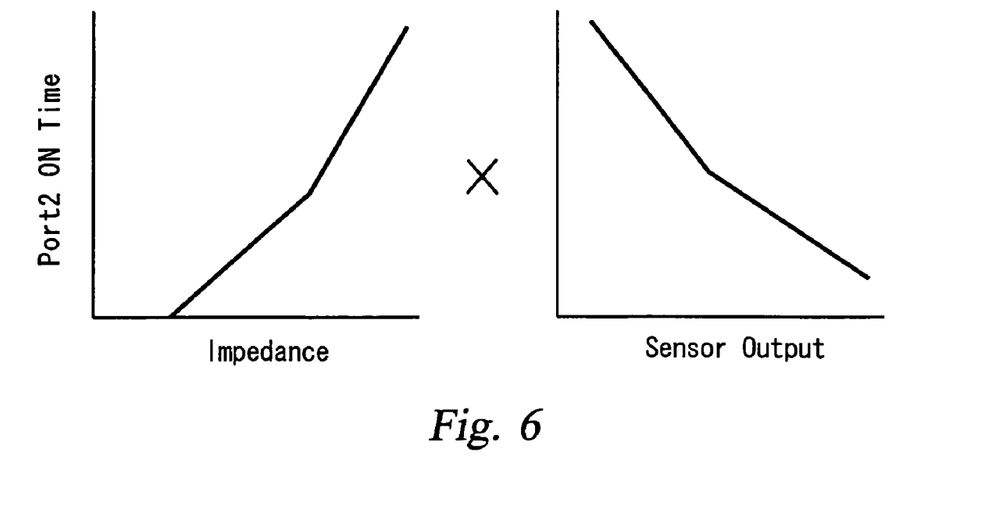
FIG. 6 illustrates the procedure to be performed in the routine shown in FIG. 5 to calculate ON time of second port.

FIG. 6 illustrates the procedure to be performed in step 106 to set the ON time for the second port 44. The left-hand drawing in FIG. 6 is a map that defines the relationship between the device impedance Rs and the ON time for the second port 44. The right-hand drawing in FIG. 6 is a map that defines the relationship between the sensor output generated by the electromotive force of the oxygen sensor 10 and the ON time for the second port 44. In step 106, the ON time values determined by these two maps are multiplied together, and the resulting time is set as the ON time for the second port 44.

According to the maps shown in FIG. 6, the greater the device impedance Rs, the longer the ON time setting for the second port 44. When the first port 24 turns ON to apply a voltage to the oxygen sensor 10, the resulting potential increases with an increase in the device impedance Rs. The higher the resulting potential, the larger the amount of electrical charge stored in the oxygen sensor 10. Therefore, the time required for forcibly releasing the electrical charge after the first port 24 is turned OFF increases with an increase in the device impedance Rs. When processing step 106 is performed, the ON time for the second port can be set to meet such requirements.

According to the maps shown in FIG. 6, the higher the sensor output generated by the oxygen sensor 10, the shorter the ON time setting for the second port 44. After the voltage application to the oxygen sensor 10 is stopped with the first port 24 turned OFF, the smaller the difference between the normal output and the output generated upon voltage application, the more quickly the sensor output of the oxygen sensor 10 reverts to the normal output. More specifically, the present embodiment causes the sensor output to quickly revert to the normal value after the first port 24 is turned OFF if the normal sensor output voltage of the oxygen sensor 10 is high. It is therefore preferred that the ON time setting for the second port 44 decrease with an increase in the normal sensor output of the oxygen sensor 10. When processing step 106 is performed, the ON time for the second port can be set to meet such preferences.

In the routine shown in FIG. 5, the ON process for the second port 44 is then performed (step 108). More specifically, step 108 is performed to keep the second port 44 ON for a period that is set in step 106. When step 108 is completed to perform the process, the sensor output of the oxygen sensor 10 reverts to the normal output, that is, the output correctly representing the oxygen concentration in the exhaust gas, immediately after the first port 24 is turned OFF.

When the sampling timing arrives again after termination of processing step 108, it is determined that the condition imposed in step 101 is not met at this time; therefore, processing step 102 is performed again. The sensor output of the oxygen sensor 10 has already reverted to the normal output level. Thus, the ECU 20 can correctly detect the sensor output corresponding to the oxygen concentration in the exhaust gas from the sampling timing arriving immediately after the device impedance Rs is calculated.

As described above, the routine shown in FIG. 5 is capable of forcibly releasing the electrical charge stored in the oxygen sensor 10 in the process for calculating the device impedance Rs by turning ON the second port 44. Further, this routine can correctly detect the information about the oxygen concentration in the exhaust gas on each sampling cycle without being affected by the voltage application for calculating the device impedance Rs. As a result, the apparatus according to the present embodiment is capable of implementing the function for correctly detecting the device impedance Rs of the oxygen sensor 10 as well as the function for accurately detecting the information about the oxygen concentration in the exhaust gas.

In the first embodiment described above, a positive voltage is applied to a positive terminal of the oxygen sensor 10 at the time of calculating the device impedance Rs, and then the potential of the positive terminal of the oxygen sensor 10 is lowered (grounded) to quickly restore the sensor output to its normal level. However, there is an alternative method for quickly restoring the sensor output to normal. More specifically, the alternative is to apply a negative voltage to a negative terminal of the oxygen sensor 10 at the time of calculating the device impedance Rs, and then to raise the potential of the oxygen sensor's negative terminal for quick restoration of the sensor output.

In the first embodiment described above, the voltage applied to the oxygen sensor 10 is reduced to zero with a view toward quickly restoring the sensor output to normal after voltage application to the oxygen 10. Alternatively, however, the voltage to be applied to the oxygen sensor 10 for quick restoration of the sensor output may be the sensor output voltage that is usually generated by the oxygen sensor 10 or may be a voltage that shifts from the usually generated output toward an opposite direction against a direction of the voltage applied to calculate the device impedance Rs.

In the first embodiment described above, the ECU 20 controls only the oxygen sensor (which generates an output that varies depending on whether the exhaust air-fuel ratio is rich or lean). However, the present invention is not limited to the control of the oxygen sensor. The present invention may also be applied to an air-fuel ratio sensor, which generates an output representing the oxygen concentration (air-fuel ratio) in a detected gas.

Second Embodiment

A second embodiment of the present invention will now be described with reference to FIGS. 7 through 9. The system according to the second embodiment can be implemented by using the configuration shown in FIG. 1 and causing the ECU 20 to execute a routine shown in FIG. 8, which will be described later, instead of the routine shown in FIG. 5.

In the first embodiment described earlier, a voltage is applied to the oxygen sensor 10 for the purpose of calculating the device impedance Rs, and then the electrical charge stored in the oxygen sensor 10 is forcibly released so as not to acquire the sensor output that incorrectly corresponds to the oxygen concentration in the exhaust gas. On the other hand, the system according to the second embodiment does not acquire the sensor output as a proper value while the sensor output is affected by voltage application to the oxygen sensor 10. In this manner, the second embodiment does not acquire the sensor output when it contains an error.

Figure 7:
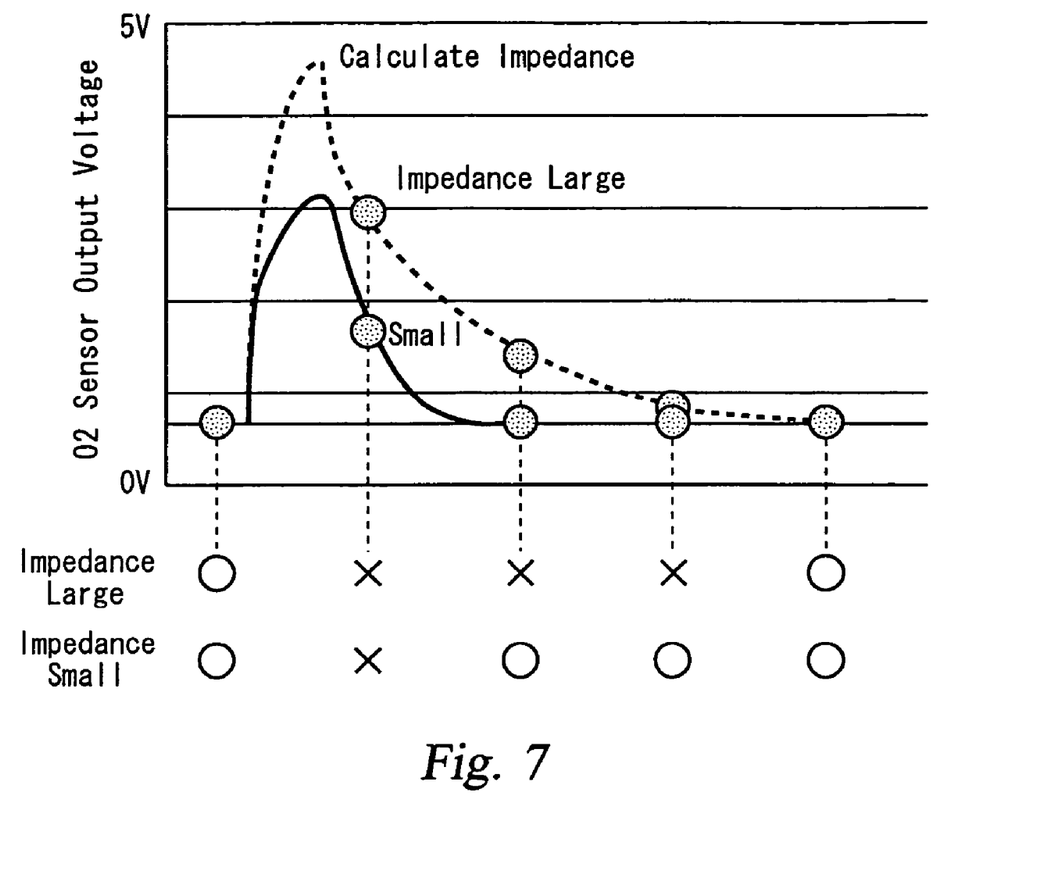
FIG. 7 shows a relationship between device impedance Rs and a waveform of sensor output that is generated before and after a voltage is applied to the oxygen sensor shown in FIG. 1.

FIG. 7 shows sensor output changes that occur before and after the voltage for calculating the device impedance Rs is applied to the oxygen sensor 10. The broken line in FIG. 7 represents a waveform that is obtained when the device impedance Rs is large and the sensor output is significantly increased upon voltage application. The solid line in FIG. 7 represents a waveform that is obtained when the device impedance Rs is small and the sensor output is insignificantly increased upon voltage application.

When the oxygen sensor 10 has a large device impedance Rs as shown in FIG. 7 (as indicated by the broken line), it takes a relatively long time for the sensor output to decrease to its inherent value, that is, a value corresponding to the oxygen concentration in the exhaust gas, after the sensor output is increased upon voltage application. Further, if the device impedance Rs of the oxygen sensor 10 is small, the sensor output reverts to its inherent value within a relatively short period of time after voltage application. Therefore, if the sensor output is sampled at fixed time intervals, the number of times the sensor output containing an error is acquired, that is, the number of times the data to be invalidated is acquired in the present embodiment, is larger when the device impedance Rs is large than when the value Rs is small. In the present embodiment, therefore, the ECU 20 applies a voltage to the oxygen sensor 10 for the purpose of calculating the device impedance Rs, and then invalidates the sampled data (sensor output) as the data containing an error by a number of times that accords to the calculated device impedance Rs.

Figure 8:
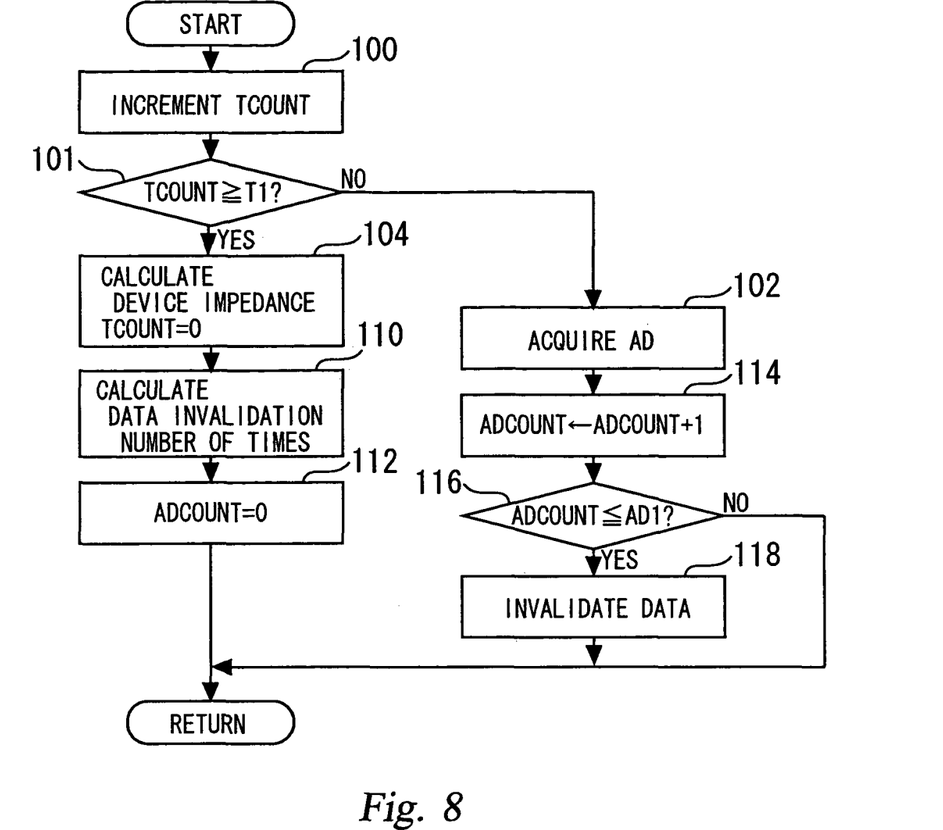
FIG. 8 is a flowchart of a control routine executed in a second embodiment of the present invention.
Figure 9:
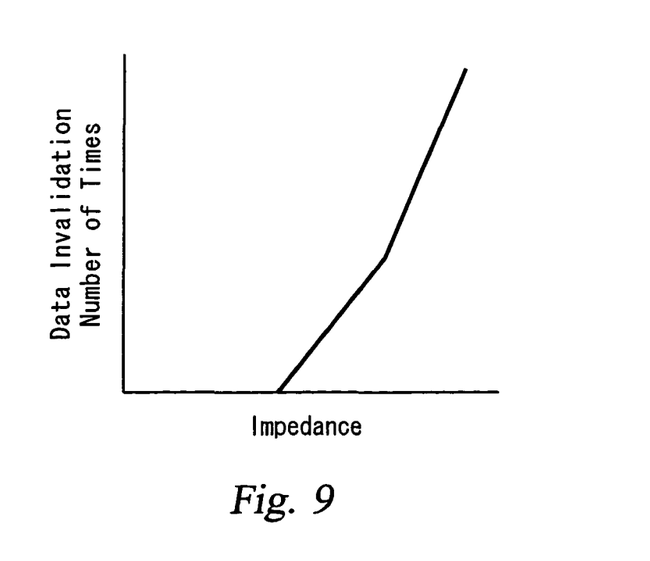
FIG. 9 shows a map of data invalidation count AD1 that is referred to in the control routine shown in FIG. 8.

FIG. 8 is a flowchart illustrating a control routine that the ECU 20 executes to implement the above functionality in accordance with the present embodiment. Like steps in FIGS. 5 and 8 are designated by like reference numerals and will be briefly described or will not be described again.

In the routine shown in FIG. 8, if it is found in step 101 that the calculation interval T1 for the device impedance Rs has elapsed (TCOUNT is greater than or equal to T1), following the processing step 104 (which calculates the device impedance Rs and clears the TCOUNT counter), data invalidation number of times AD1 is calculated (step 110). FIG. 9 shows a typical map that defines the relationship between the data invalidation number of times AD1 and the device impedance Rs. The ECU 20 stores a map, which looks like the one shown in FIG. 9. Step 110 is performed to reference the map and calculate the data invalidation number of times that corresponds to the device impedance Rs calculated in step 104. According to the map shown in FIG. 9, the larger the device impedance Rs is, thus the more likely the effect of the voltage application is remained in the sensor output, the higher the data invalidation number of times AD1 is set.

Next, the routine shown in FIG. 8 performs a process for clearing the ADCOUNT counter (step 112). The ADCOUNT counter counts the number of times the sensor output is sampled after the calculation process for the device impedance Rs. Upon completion of processing step 112, the ECU 20 terminates the current processing cycle.

If it is found in step 101 that TCOUNT is less than T1, after sampling the sensor output in step 102, the routine shown in FIG. 8 increments the ADCOUNT counter (step 114). According to the above increment process, it is possible to sample the sensor output as well as to increment the ADCOUNT counter upon every sampling interval (upon every routine startup) until elapse of the device impedance calculation interval T1 is determined.

Next, the routine shown in FIG. 8 judges whether the count reached by the ADCOUNT counter is not greater than the data invalidation count AD1 (step 116). If it is judged that ADCOUNT is less than or equal to AD1, the sensor output (data) sampled in step 102 is invalidated (step 118). When it is found that ADCOUNT is greater than AD1, processing step 118 is skipped so that the current processing cycle terminates without invalidating the acquired data.

As described above, the routine shown in FIG. 8 can invalidate the sampled sensor output by a specified data invalidation number of times AD1 after a voltage is applied to the oxygen sensor 10 for the purpose of calculating the device impedance Rs. The data invalidation number of times AD1 can be set in accordance with the device impedance Rs so that it corresponds to a period during which an error will be superposed over the sensor output. Therefore, the system according to the present embodiment is capable of implementing the function for calculating the device impedance Rs of the oxygen sensor 10 as well as the function for constantly detecting the information about the oxygen concentration in the exhaust gas with high accuracy.

In the second embodiment described above, the data invalidation number of times AD1 is set in accordance with the device impedance Rs of the oxygen sensor 10. However, there is an alternative method for setup. For AD1 setup purposes, the normal sensor output value of the oxygen sensor 10 may alternatively be taken into account as is the case with the first embodiment. More specifically, the smaller the difference between the normal sensor output value of the oxygen sensor 10 and the sensor output value attained upon voltage application, thus the more likely the time required for data convergence is to be short, the lower the data invalidation number of times can be set.

In the second embodiment described above, the ECU 20 controls only the oxygen sensor (which generates an output that varies depending on whether the exhaust air-fuel ratio is rich or lean). However, the present invention is not limited to the control of the oxygen sensor. The present invention may also be applied to an air-fuel ratio sensor, which generates an output representing the oxygen concentration (air-fuel ratio) in a detected gas.

Third Embodiment

A third embodiment of the present invention will now be described with reference to FIGS. 10A, 10B and 11. The system according to the third embodiment can be implemented by using the configuration shown in FIG. 1 and causing the ECU 20 to execute a routine shown in FIG. 11, which will be described later, instead of the routine shown in FIG. 5.

In the present embodiment, the ECU 20 performs a process for calculating the device impedance Rs each time the device impedance calculation interval T1 elapses, as is the case with the first embodiment. When the device impedance Rs is to be calculated, a voltage is applied to the oxygen sensor 10 as described earlier. The output of the oxygen sensor 10 does not accurately correspond to the oxygen concentration in the exhaust gas until the influence of voltage application disappears. Therefore, the information about the oxygen concentration in the exhaust gas can be accurately detected in accordance with the sensor output only during the time interval between the instant at which the effect of the voltage application in the sensor output disappears and the instant at which the device impedance calculation interval T1 elapses.

The time required for the influence of voltage application upon the sensor output of the oxygen sensor 10 to disappear increases with an increase in the device impedance Rs. Therefore, if the device impedance calculation interval T1 is fixed, although a sufficient period for correctly detecting the information about the oxygen concentration in the exhaust gas can be acquired as far as the device impedance Rs is low, such a period cannot be acquired in a situation where the device impedance Rs is high.

Figure 10A:
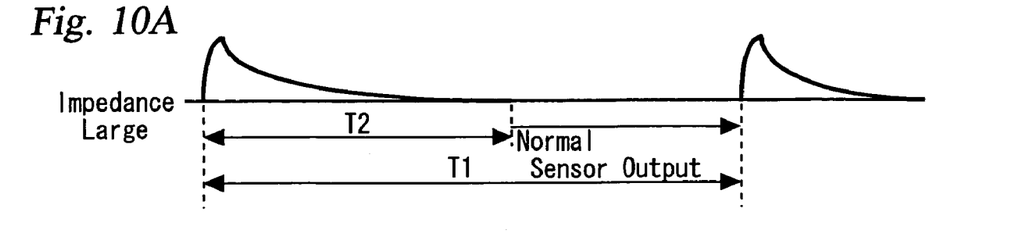
FIGS. 10A and 10B are timing diagrams illustrating an outline of an operation that is performed in a third embodiment of the present invention.
Figure 10B:
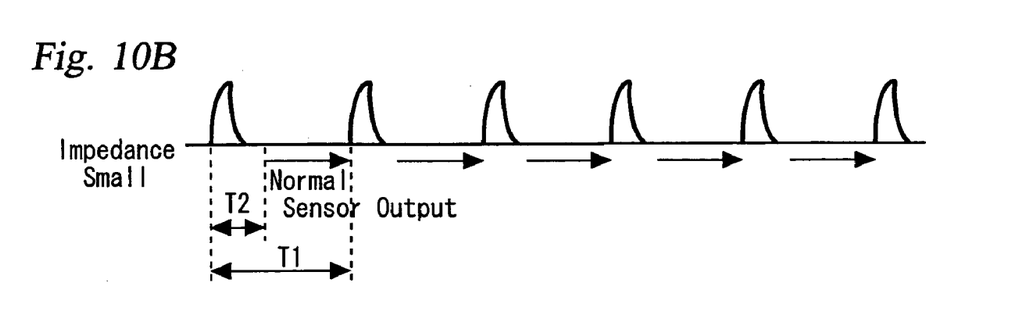

FIGS. 10A and 10B are timing diagrams illustrating the operations that the present embodiment performs to handle the above situation. Waveform shown in FIG. 10A represents the sensor output that the oxygen sensor 10 generates when the device impedance Rs is high. Waveform shown in FIG. 10B represents the sensor output that the oxygen sensor 10 generates when the device impedance Rs is low. In FIGS. 10A and 10B, the period shown with T1 designates the above-mentioned device impedance calculation interval. The period shown with T2 designates a period during which sensor output sampling is prohibited.

As indicated in FIG. 10A, the system according to the present embodiment sets a long device impedance calculation interval T1 and a long sampling prohibition period T2 if the device impedance Rs is high. If, on the other hand, the device impedance Rs is low, the system sets a short device impedance calculation interval T1 and a short sampling prohibition period T2 as indicated in FIG. 10B. When the values T1 and T2 are set in this manner, an adequate period can be obtained for normal sensor output acquisition without regard to the length of the period that is required for the influence of voltage application for calculating the device impedance Rs upon the sensor output to disappear. As a result, the system according to the present embodiment can properly detect the information about the oxygen concentration in the exhaust gas at all times without regard to the device impedance Rs of the oxygen sensor 10.

Figure 11:
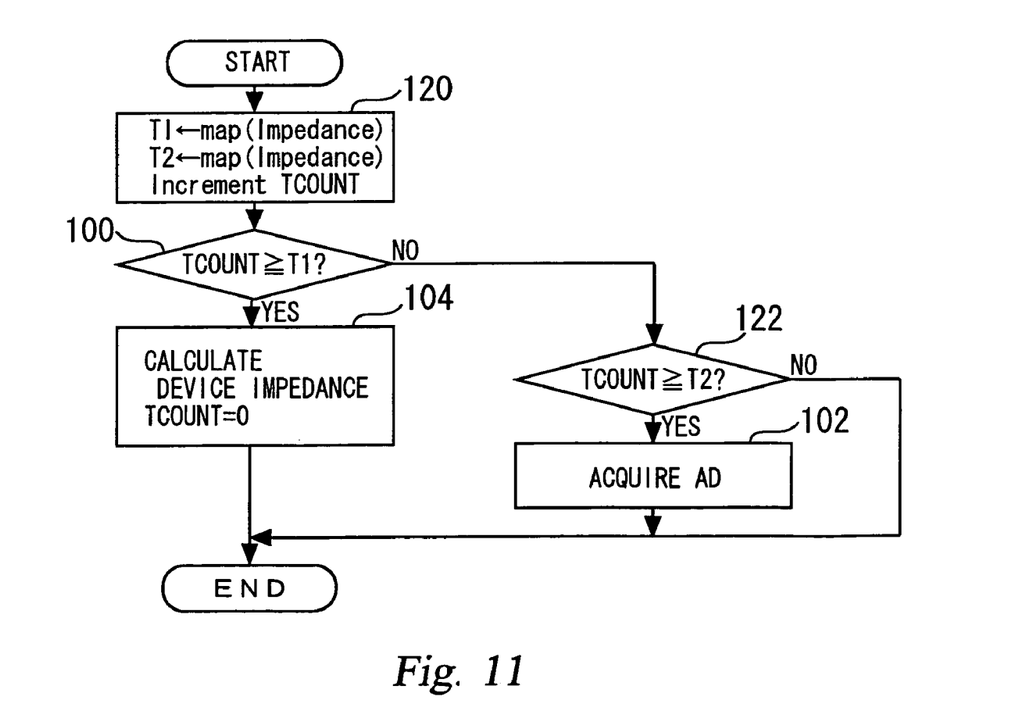
FIG. 11 is a flowchart of a control routine executed in the third embodiment of the present invention.

FIG. 11 is a flowchart illustrating a control routine that the ECU 20 executes to implement the above functionality. Like steps in FIG. 11 and FIG. 5 or 8 are designated by like reference numerals and will be briefly described or will not be described again.

The routine shown in FIG. 11 first increments the TCOUNT counter and sets the device impedance calculation interval T1 and the sampling prohibition period T2 (step 120). In the present embodiment, the ECU 20 stores a map for defining the value T1 in relation to the device impedance Rs and a map for defining the value T2. In step 120, these maps are referenced to set the values T1 and T2.

Upon termination of processing step 120, processing step 100 is performed to judge whether TCOUNT is greater than or equal to T1. If it is found that TCOUNT is greater than or equal to T1, step 104 is performed to calculate the device impedance Rs and clear the TCOUNT counter, and then the current processing cycle comes to an end. If, on the other hand, it is found that TCOUNT is less than T1, step 122 is performed to judge whether TCOUNT is greater than or equal to T2.

If it is found that TCOUNT is not greater than or equal to T2, it can be judged that the sampling prohibition period T2 has not yet elapsed after calculation of the device impedance Rs. In this instance, the routine shown in FIG. 11 terminates the current processing cycle thereafter without sampling any sensor output. If, on the other hand, it is found that TCOUNT is greater than or equal to T2, it can be judged that the sampling prohibition period T2 has already elapsed. In this instance, step 102 is performed thereafter to sample the sensor output, and then the current processing cycle comes to an end. According to the process described above, the sensor output can be acquired at every sampling time interval only after the end of the sampling prohibition period T2 and before the end of the device impedance calculation interval T1.

The T1-related map and T2-related map for use in step 120 are both set so that the higher the device impedance Rs, the greater the value T1 or T2. More specifically, the map concerning the device impedance calculation interval T1 defines the relationship between the values Rs and T1 so that a time period in which the oxygen sensor 10 can generate normal sensor output is always sufficiently acquired without regard to the value of the device impedance Rs. Further, the map concerning the sampling prohibition period T2 defines the relationship between the value T2 and the device impedance Rs so that the sampling prohibition period T2 is equal to a period during which the sensor output of the oxygen sensor 10 remains affected by voltage application. Therefore, the routine shown in FIG. 11 can always provide a sufficient period for normal output generation by the oxygen sensor 10 without regard to the value of the device impedance Rs, and sample correct sensor outputs only. Therefore, the system according to the present embodiment is capable of implementing the function for accurately detecting the device impedance Rs as well as the function for accurately detecting the information about the oxygen concentration in the exhaust gas.

In the third embodiment described above, the device impedance calculation interval T1 and the sampling prohibition period T2 are set in accordance with the device impedance Rs. However, there is an alternative method for such setup. Setup may alternatively be performed while considering the normal sensor output value of the oxygen sensor 10, as is the case with the first embodiment. More specifically, the smaller the difference between the normal sensor output value of the oxygen sensor 10 and the sensor output value attained upon voltage application, i.e., the more likely the time required for data convergence is to be short, the lower the T1 and T2 can be set.

In the third embodiment described above, the ECU 20 controls only the oxygen sensor (which generates an output that varies depending on whether the exhaust air-fuel ratio is rich or lean). However, the present invention is not limited to the control of the oxygen sensor. The present invention may also be applied to an air-fuel ratio sensor, which generates an output representing the oxygen concentration (air-fuel ratio) in a detected gas.

Fourth Embodiment

A fourth embodiment of the present invention will now be described with reference to FIGS. 12 through 15. The system according to the fourth embodiment can be implemented by using the apparatus according to the third embodiment and causing the ECU 20 to execute a routine shown in FIG. 14, which will be described later, instead of the routine shown in FIG. 11.

Figure 12:
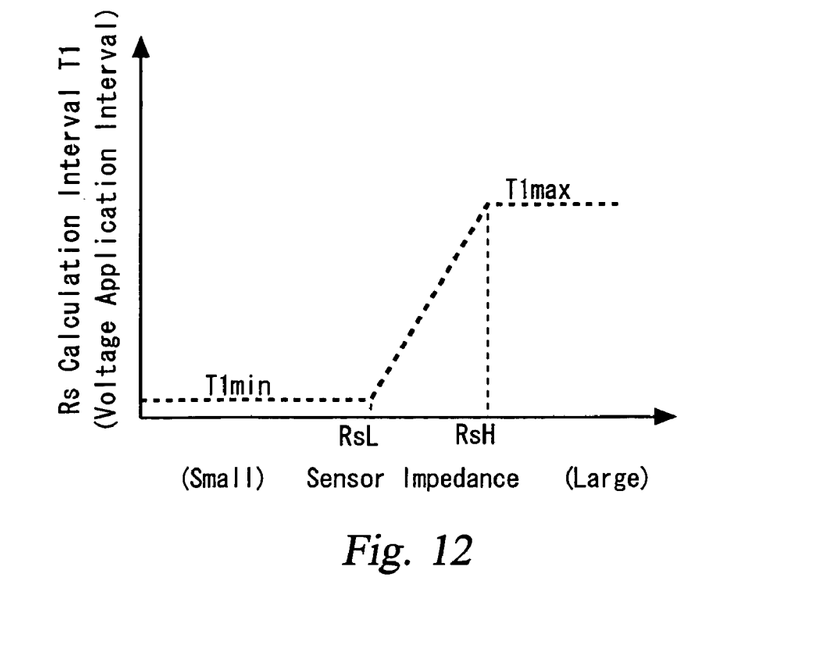
FIG. 12 shows a typical map of the device impedance calculation interval T1 that can be used in the third embodiment of the present invention.

As described earlier, the apparatus according to the third embodiment increases the device impedance calculation interval T1 with an increase in the device impedance Rs. FIG. 12 shows a typical map of the device impedance calculation interval T1 that can be used with the apparatus according to the third embodiment (see step 120 in FIG. 11). According to this map, in a region where the device impedance Rs is between the high convergence value RsH and the low convergence value RsL, the device impedance calculation interval T1 is determined so that it is linear in relation to the device impedance Rs. In a region where the device impedance Rs is above the high convergence value RsH or below the low convergence value RsL, however, the resulting determined device impedance calculation interval T1 coincides with a specified maximum value T1max or minimum value T1min. According to such a map, the intervals at which the voltage for detecting the device impedance Rs is applied to the oxygen sensor 10 increase with an increase in the device impedance Rs and decrease with a decrease in the device impedance Rs.

Figure 13:
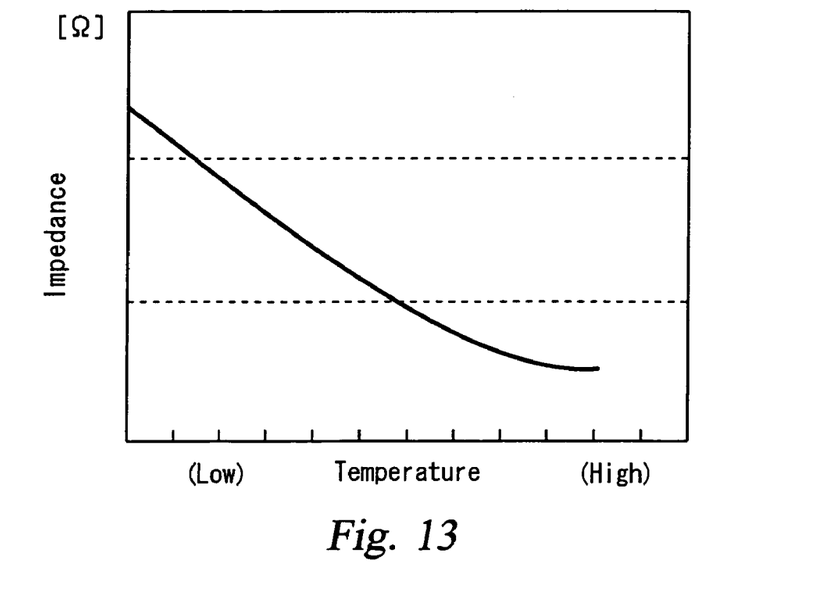
FIG. 13 shows a relationship between device temperature and device impedance Rs of the oxygen sensor shown in FIG. 1.

FIG. 13 illustrates the relationship between the device temperature and device impedance Rs of the oxygen sensor 10. As indicated in this figure, the device impedance Rs decreases with an increase in the device temperature of the oxygen sensor. When the voltage for device impedance detection is applied to the oxygen sensor 10, the current I flowing to the oxygen sensor 10 increases with a decrease in the device impedance Rs. Therefore, the current I increases with an increase in the device temperature of the oxygen sensor 10.

According to the map shown in FIG. 12, the device impedance calculation interval T1 is set to the minimum value when the device impedance Rs is below the low convergence value RsL, that is, when a large current I flows upon voltage application. In such an instance, since the device impedance Rs is frequently detected, it becomes that a large current I frequently flows through the oxygen sensor 10. The larger the current I flowing through the oxygen sensor 10 is and the longer the period of time during which the current I flows, the greater the damage caused to the oxygen sensor 10 will be. Therefore, if the device impedance calculation interval T1 is determined in accordance with the map shown in FIG. 12, it is likely that the oxygen sensor 10 will be significantly damaged after the device temperature is adequately raised. Under these circumstances, the present embodiment employs a long device impedance calculation interval T1 to decrease the frequency of voltage application to the oxygen sensor 10 in a region where the device impedance Rs is sufficiently low.

Figure 14:
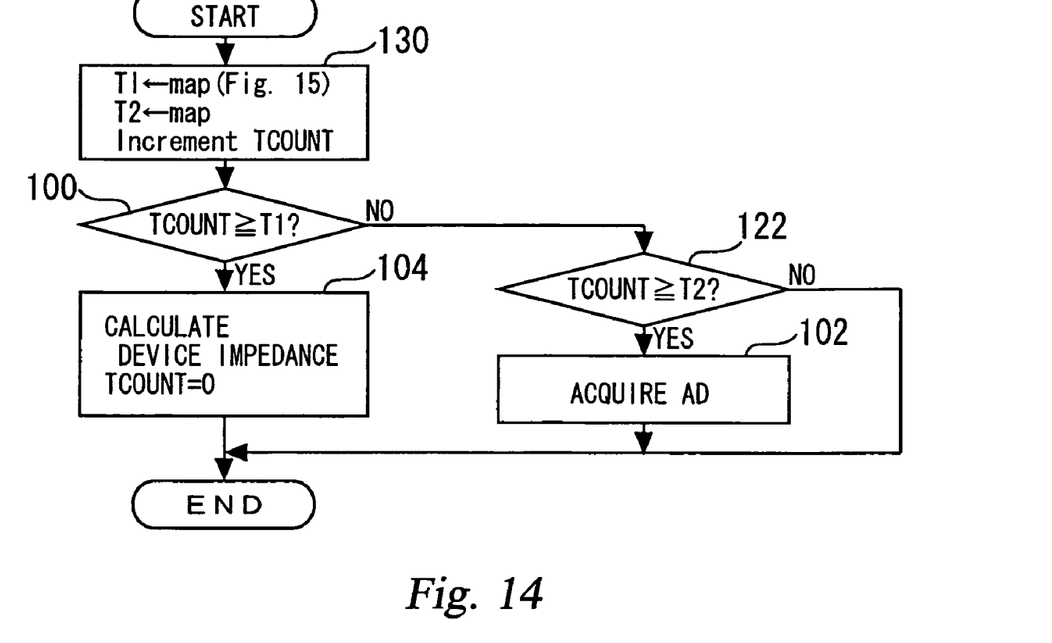
FIG. 14 is a flowchart of a control routine executed in a fourth embodiment of the present invention.

FIG. 14 is a flowchart illustrating a control routine that the ECU 20 according to the present embodiment performs in order to implement the above functionality. The routine shown in FIG. 14 is the same as the routine shown in FIG. 11 except that step 120 is replaced by step 130. Like steps in FIG. 14 and FIG. 11 are designated by like reference numerals and will be briefly described or will not be described again.

In the routine shown in FIG. 14, step 130 is performed to a) increment the TCOUNT counter, b) set the device impedance calculation interval T1, and c) set the sampling prohibition period T2. Processes a) and c) are performed by the same method as in the third embodiment (see step 120 in FIG. 11). Process b) is performed to set the device impedance calculation interval T1 by referencing the map shown in FIG. 15.

Figure 15:
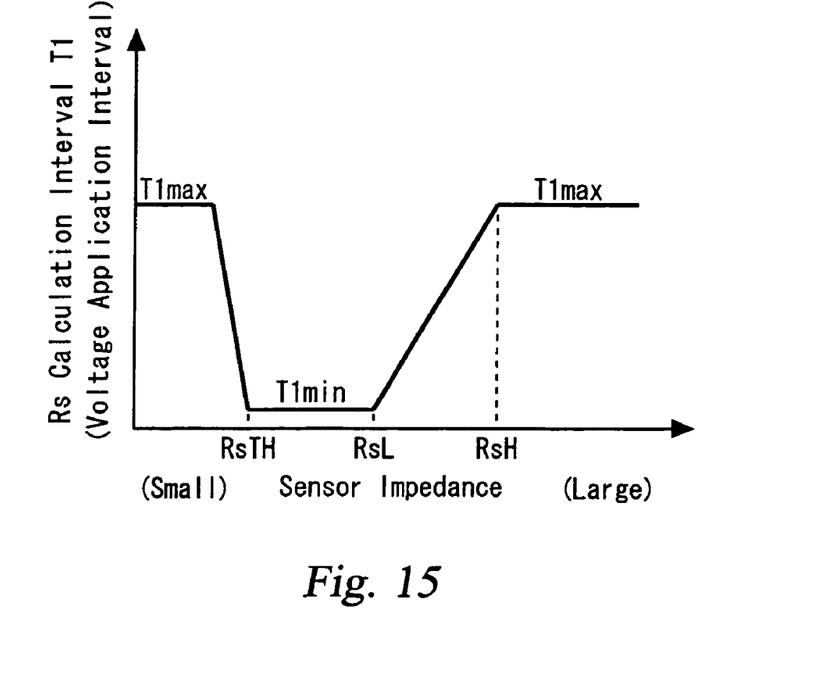
FIG. 15 shows a map of device impedance calculation interval T1 that is referred to in the control routine shown in FIG. 14.

The FIG. 15 shows a typical map that the ECU 20 stores in order to set the device impedance calculation interval T1. A specified threshold value RsTH, which is smaller than the low convergence value RsL, is set on the horizontal axis of the map shown in FIG. 15. Within a region where the device impedance Rs is above the threshold value RsTH, this map is designed in the same manner as the map shown in FIG. 12 is. Within a region where the device impedance Rs is below the threshold value RsTH, the map shown in FIG. 15 is designed so that the device impedance calculation interval T1 promptly reaches the maximum value T1max when the sensor impedance Rs decreases.

The threshold value RsTH shown in FIG. 15 is defined as the smallest device impedance Rs that does not cause any undue damage to the oxygen sensor 10 when the device impedance calculation interval T1 is set to the minimum value T1min. In other words, the map shown in FIG. 15 sets the device impedance calculation interval T1 to the minimum value T1min when the device impedance Rs of the oxygen sensor 10 is RsTH. In this instance, the voltage for device impedance detection is repeatedly applied to the oxygen sensor 10 at intervals of the minimum value T1min. Upon each voltage application, the current I (=V/RsTH) obtained by dividing the applied voltage V by the value RsTH flows to the oxygen sensor 10. The threshold value RsTH represents the device impedance Rs for generating the largest current I that can repeatedly flow at intervals of T1min without causing any undue damage to the oxygen sensor 10.

The routine shown in FIG. 14 repeatedly performs a process for detecting the device impedance Rs at device impedance calculation intervals T1 that is set in accordance with the map shown in FIG. 15. In this instance, the damage caused to the oxygen sensor 10 upon voltage application is maximized when the device impedance Rs coincides with the threshold value RsTH, due to the relationship between the voltage application intervals (T1) and the current I generated upon the voltage application. As described earlier, the threshold value RsTH is set so that the oxygen sensor 10 does not receive any undue damage in such an instance. In the present embodiment, therefore, a repeated execution of the process for detecting the device impedance Rs will not unduly damage the oxygen sensor 10 without regard to the value of the device impedance Rs.

As described above, the apparatus according to the present embodiment can protect the oxygen sensor 10 from undue damage by decreasing the frequency of device impedance detection within a region where the device impedance Rs of the oxygen sensor 10 is sufficiently low. As a result, the apparatus according to the present embodiment adequately prevents the oxygen sensor 10 from deteriorating while providing the same advantages as the apparatus according to the third embodiment.

The present invention, which is configured as described above, provides the following advantages.

According to a first aspect of the present invention, the gas concentration sensor's output can converge to the voltage generated by the gas concentration sensor itself, that is, the output corresponding to the exhaust air-fuel ratio immediately after the impedance detection voltage is applied to the gas concentration sensor. Therefore, the present invention can implement the function for detecting the device impedance and the function for accurately detecting the information about the exhaust air-fuel ratio.

According to a second aspect of the present invention, the greater the device impedance of the gas concentration sensor is, thus the longer the period of time for the influence of the impedance detection voltage to disappear, the longer the period (specified period) of voltage application for canceling the influence can be. Therefore, the present invention can efficiently negate the influence of the impedance detection voltage within a short period of time.

According to a third aspect of the present invention, the smaller the difference between the voltage generated by the gas concentration sensor itself and the impedance detection voltage is, thus the influence of the impedance detection voltage is more likely to disappear in a short time, the shorter the period (specified period) of voltage application for canceling the influence can be. Therefore, the present invention can efficiently negate the influence of the impedance detection voltage within a short period of time.

According to a fourth aspect of the present invention, the gas concentration sensor's output can be invalidated during a specified period of time during which the gas concentration sensor's output is affected by the impedance detection voltage. Therefore, the present invention can implement the function for detecting the device impedance and the function for accurately detecting the information about the exhaust air-fuel ratio.

According to a fifth aspect of the present invention, the greater the device impedance of the gas concentration sensor is, thus the longer the period of time during which the influence of the impedance detection voltage remains, the longer the data invalidation period (specified period) can be. Therefore, the present invention can effectively avoid erroneous detection of the exhaust air-fuel ratio, which is based on the gas concentration sensor's output.

According to a sixth aspect of the present invention, the greater the device impedance of the gas concentration sensor is, the longer the time intervals (specified time intervals) at which the impedance detection voltage is applied can be. Without regard to the magnitude of the device impedance, therefore, the present invention can properly provide a period during which the gas concentration sensor's output correctly corresponds to the exhaust air-fuel ratio.

According to a seventh aspect of the present invention, the output acquisition period can begin at the end of a period (specified period) during which the gas concentration sensor's output is affected by the impedance detection voltage. Further, the greater the device impedance is, thus the longer the period of time during which the influence of the impedance detection voltage remains, the longer the above-mentioned specified period can be. Without regard to the magnitude of the device impedance, therefore, the present invention can recognize a period during which the gas concentration sensor's output correctly corresponds to the exhaust air-fuel ratio as an output acquisition period.

According to an eighth aspect of the present invention, the time intervals (specified intervals) at which the impedance detection voltage is applied can be longer in a situation where the device impedance is below a predefined threshold value than in a situation where the device impedance coincides with the predefined threshold value. In other words, in a situation where a large current flows upon impedance detection because of low device impedance, the present invention can decrease the frequency of device impedance detection. Therefore, the present invention effectively prevents the gas concentration sensor from being excessively damaged in a situation where the device impedance is low.

Further, the present invention is not limited to these embodiments, but variations and modifications may be made without departing from the scope of the present invention. The entire disclosure of Japanese Patent Application No. 2003-285183 filed on Aug. 1, 2003 including specification, claims, drawings and summary are incorporated herein by reference in its entirety.

The invention claimed is:

1. A controller for a gas concentration sensor that generates an output correlating with the oxygen concentration in a detected gas, said controller comprising:
impedance detection means for applying an impedance detection voltage to said gas concentration sensor to detect a device impedance of said gas concentration sensor;
data invalidation means for invalidating the output of said gas concentration sensor for a specified period of time after said impedance detection voltage is applied to said gas concentration sensor; and
data invalidation period setup means for increasing said specified period of time with an increase in said device impedance.

* * * * *

UNITED STATES PATENT AND TRADEMARK OFFICE
CERTIFICATE OF CORRECTION

PATENT NO. : 7,846,313 B2
APPLICATION NO. : 12/005266
DATED : December 7, 2010
INVENTOR(S) : Kenji Tashiro et al.

It is certified that error appears in the above-identified patent and that said Letters Patent is hereby corrected as shown below:

Title page Item (75) please replace "Kenji Tashiro, Susuno (JP)" with --Kenji Tashiro, Susono (JP).--

Signed and Sealed this
Twenty-sixth Day of April, 2011

David J. Kappos
*Director of the United States Patent and Trademark Office*